United States Patent [19]

Frey et al.

[11] Patent Number: 4,938,772
[45] Date of Patent: Jul. 3, 1990

[54] FEMORAL PROSTHESIS

[75] Inventors: Otto Frey, Winterthur; Rudolf Kock, Berlingen, both of Switzerland

[73] Assignee: Sulzer Brothers Limited, Winterthur, Switzerland

[21] Appl. No.: 416,513

[22] Filed: Oct. 3, 1989

[30] Foreign Application Priority Data

Oct. 26, 1988 [CH] Switzerland .................... 3985/88

[51] Int. Cl.⁵ .................... A61F 2/36; A61F 2/30
[52] U.S. Cl. .................... 623/23; 623/18
[58] Field of Search .................... 623/16, 18, 20-23

[56] References Cited

U.S. PATENT DOCUMENTS

| | | | |
|---|---|---|---|
| 4,536,894 | 8/1985 | Galante | 623/22 |
| 4,636,219 | 1/1987 | Pratt et al. | 623/18 X |
| 4,660,755 | 4/1987 | Farling et al. | 623/18 X |
| 4,718,915 | 1/1988 | Epinette | 623/23 |
| 4,753,657 | 6/1988 | Lee et al. | 623/23 X |

FOREIGN PATENT DOCUMENTS

| | | | |
|---|---|---|---|
| 0149527 | 7/1985 | European Pat. Off. | 623/23 |
| 0196258 | 10/1986 | European Pat. Off. | 623/23 |
| 0217034 | 4/1987 | European Pat. Off. | 623/23 |
| 0266081 | 5/1988 | European Pat. Off. | |
| 0273871 | 7/1988 | European Pat. Off. | 623/23 |

Primary Examiner—Ronald L. Frinks
Attorney, Agent, or Firm—Kenyon & Kenyon

[57] ABSTRACT

The prosthesis stem is provided with a recess on each side having boundary walls concentric to a common center of curvature. Each recess receives a molding which carries a wire mesh structure for the invasion of bone tissue after implantation. Bending of the proximal zone of the stem occurs without movement of the molding so that shear stresses are not imposed upon the bone tissue invading the wire mesh. A peg-like projection on each molding fits with a clearance in a further recess in the metal stem to avoid accidental sliding out of each recess.

12 Claims, 1 Drawing Sheet

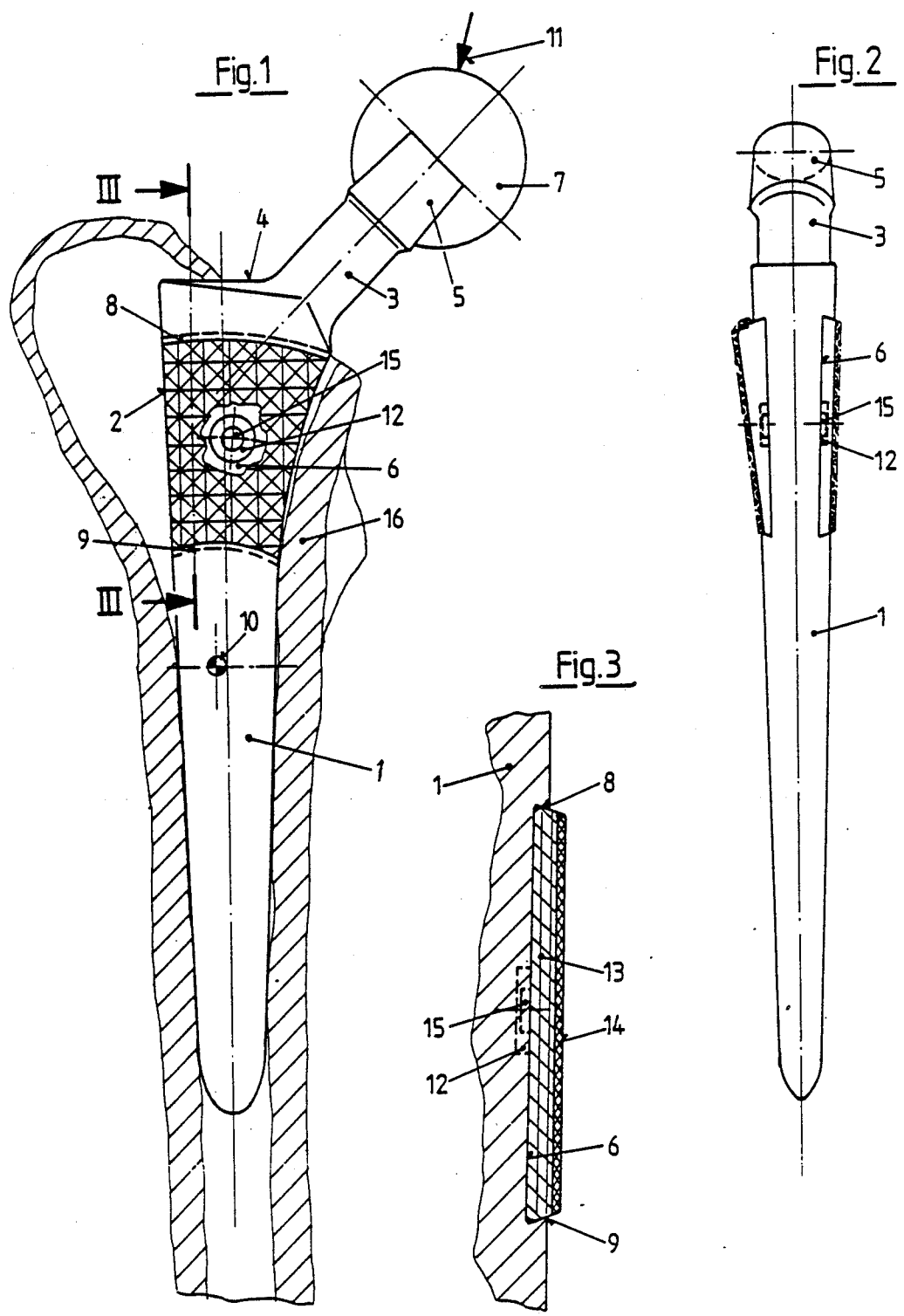

FEMORAL PROSTHESIS

This invention relates to a femoral prosthesis. More particularly, this invention relates to a blade-like metal stem for a femoral head prosthesis.

As is known, various types of blade-like metal stems have been provided for the anchoring of a femoral head prosthesis in a femur. In some cases, the stems have been provided with inserts and/or wedge-like constructions for mounting in a femur such as described in European Patent Applications Nos. 0 196 258; 0 149 527 and 0 266 081 as well as French Patent No. 2 610 824. In other cases, such as described in European Patent Application No. 0 273 871 a femoral neck hip prosthesis stem is provided with at least one recess forming a seat for receiving one of a number of modular inserts of different shapes and sizes by means of which a composite prosthesis is made suitable for a left hip or a right hip. As described, the inserts may be coupled within recesses by means of dovetail notches to obtain a stable and secure mechanical inter-connection of the inserts to the stem.

European Patent Application No. 0 127 034 describes a stem having a surface structure adapted for the ingrowth and/or invasion of bone tissue in a proximal zone. In this respect, recesses are provided in the stem in which guides are disposed and into which separate plastic moldings can be introduced. These moldings serve to make up the external shape of the stem in the proximal zone and are covered by a single layer or multi-layer metal mesh, particularly a wire mesh.

When a stem of this kind is implanted in an uncemented manner in a bone, there is a direct boundary surface between the bone tissue and the metal mesh structure which the bone tissue is able to invade. However, shear forces are produced in the boundary surface and serve to stress the tissue growing through this boundary surface when the stem experiences bending stresses.

Accordingly, it is an object of the invention to provide a blade-like metal stem with a surface structure for the invasion of bone tissue in which shear forces are not produced during bending of the stem.

It is another object of the invention to be able to accommodate bending of a femoral prosthesis stem whithout introducing shear forces in bone tissue invading a porous structure in a proximal zone of the stem.

Briefly, the invention provides a femoral prosthesis which is comprised of a metal stem having a recess in a proximal zone of each of two opposite sides, at least one plastic molding inserted in each recess and at least one layer of wire mesh in each molding for an ingrowth of tissue.

In accordance with the invention, each recess in the metal stem has a proximal boundary wall and a distal boundary wall, both of which are disposed on concentric arcs having a common center of curvature distal of the walls. In addition, each molding has curved surfaces slidably engaging the walls of a respective recess. In this respect, the walls of the recess are effective as guides for the moldings.

After implantation and ingrowth of tissue in the wire meah layers on the plastic moldings, any forces which act on a joint head of the prosthesis eccentrically of the stem axis and which produce bending stresses on the stem cause relative movements between the plastic moldings and the metal stem. These relative movements are "rotations" of the moldings relative to the stem, the rotation being guided by the concentric walls of the recesses. Thus, the back of each molding and the surface of the stem recess shift relative to one another while relative movements in the boundary surface between the bone tissue and the surface structure of the moldings are at least very substantially reduced. Hence, shear stresses which would otherwise be damaging to the tissue do not occur in the boundary surface.

In order to reduce the stressing of the boundary surface between the wire mesh and the bone tissue, the walls defining the recesses in the metal stem conveniently extend laterally to medially over the entire side of the stem. In order to prevent the molding from accidentally slipping out of the recesses, each recess is provided with a further second recess while a peg-like projection is provided on each molding for fitting into the second recess, foe example with some clearance.

So that the stem may be used without alterations for operation cavities of different sizes in the femur and/or for both left and right hip joints, moldings of different thickness are conveniently made available with the thickness of each individual "size" possibly increasing distally to proximally. These and other objects and advantages of the invention will become more apparent from the following detailed description taken in conjunction with the accompanying drawings wherein:

FIG. 1 illustrates a side view of from frontal-to-dorsal of a metal stem of a femoral prosthesis in accordance with the invention;

FIG. 2 illustrates a side view of the prosthesis of FIG. 1; and

FIG. 3 illustrates a view taken on line III—III of a molding inserted in a recess of the metal stem of the prosthesis of FIG. 1. Referring to FIGS. 1 and 2, the femoral prosthesis is constructed in generally known manner so as to have a straight stem 1 which can be introduced into a femur 16 which narrows distally. As indicated, the stem 1 merges at the proximal end into a neck 3 by way of a horizontal shoulder 4 at the lateral narrow side. The neck 3, in turn, merges into a conical peg 5 which is adapted to receive a femoral head 7 shown only in outline in FIG. 1.

The metal stem 1 is formed on both sides with a recess 6 in the proximal zone. Each recess 6 has a proximal boundary wall 8 and a distal boundary wall 9. These walls 8, 9 are in the form of concentric circular arcs having a common center of curvature 10 distal of the walls 8, 9, for example, at the fulcrum of the flexions of the stem 1 caused by stressing of the femoral head 7 in the direction indicated by the arrow 11 in FIG. 1. As illustrated in FIG. 3, each wall 8, 9 of the recess is inclined inwardly so as to define a recess of dove-tail cross-section. Each recess 6 also has a further second recess 12 of circular shape in the base thereof.

Referring to FIG. 3, each recess 6 is provided with at least one plastic molding 13. As indicated in FIG. 2, each molding 13 is adapted medially and laterally to the stem shape and increases in thickness distally to proximally.

Referring to FIG. 3, each molding 13 is made of plastic and has a surface structure on the outside surface, for example, in the form of a single layer or multi-layer metal mesh or wire mesh 14. In addition, as indicated in FIG. 3, each molding 13 widens conically in order to engage in the recess 6 bounded by the walls 8, 9.

In order to prevent a molding 13 from accidentally slipping out of a recess 6, each molding 13 is provided with a peg-like projection 15 which engages with a clearance in the recess 12 (see FIG. 3).

As can be seen in FIG. 2, the moldings 13 can be different thickness so that a thick molding can be introduced into one side of the stem and a thin molding on the other side. This enables the same stem to be used for operation cavities of different sizes and/or for both left and right hips.

Referring to FIG. 1, after the prosthesis has been implanted, for example, in an uncemented manner in the femur 16, bone tissue may grow into the mesh 14 on each side of the stem 1. Thereafter, should any eccentric load be imposed upon the head 7, for example, in the direction indicated by the arrow 11, the proximal zone of the stem 1 is able to bend, for example to the right as viewed, while the moldings 13 remain in place. That is, the proximal zone of the stem 1 is able to move relative to the moldings 13 with the relative sliding of the moldings 13 in the respective recesses 6. As a result, shear stresses are not imposed upon the bone tissue within the boundary surface between the bone tissue and the metal mesh 14. When the load is relieved, the stem 1 is able to bend in a reverse direction into the position indicated in FIG. 1.

The invention thus provides a metal stem for a femoral prosthesis in which the bending of the proximal zone of the prosthesis under loading does not stress invading tissue produced in a boundary surface between a wire mesh insert and adjacent bone tissue.

What is claimed is:

1. A femoral prosthesis comprising:
   a metal stem having a recess in a proximal zone of each of two opposite sides thereof, each recess having a proximal boundary wall and a distal boundary wall, said walls being disposed an concentric arcs having a common center of curvature distal of said walls;
   at least one plastic molding inserted in each recess, each molding having curved surfaces engaging said walls of a respective recess; and
   a surface structure on each molding for an ingrowth of tissue.

2. A prosthesis as set forth in claim 1 wherein each wall extends laterally to medially over an entire side of said stem.

3. A femoral prosthesis as set forth in claim 1 which further comprises a second recess within each recess of said stem and a peg-like projection on each molding fitting into second recess.

4. A femoral prosthesis as set forth in claim 1 wherein said molding on one side said stem is of different thickness from said molding on the other side of said stem.

5. A femoral prosthesis as set forth in claim 4 wherein each molding is of increasing thickness in a proximal direction.

6. A femoral prosthesis as set forth in claim 1 wherein each molding is of increasing in a proximal direction.

7. A femoral prosthesis as set forth in claim 1 wherein each recess is of dove-tail cross-section and slidably receives a respective plastic molding therein.

8. A femoral prosthesis as set forth in claim 7 which further comprises a second recess with each recess of said stem and a peg-like on each molding fitting into said second recess.

9. A femoral prosthesis comprising
   a metal stem having a recess in a proximal zone on at least one side thereof, said recess having a proximal boundary wall and a distal boundary wall, said walls being disposed an concentric ars having a common center of curvature distal of said walls;
   at least one plastic molding inserted in said recess, each molding having curved surfaces slidably engaging said walls of a respective recess; and
   a surface structure on each molding for an ingrowth of tissue.

10. A prosthesis as set forth in claim 9 wherein each wall extends laterally to medially over an entire side of said stem.

11. A femoral prosthesis as set forth in claim 10 which further comprises a second recess with said recess of said stem and a peg-like projection on said molding fitting into said second recess with a clearance.

12. A femoral prosthesis as set forth in claim 10 wherein said recess is of dove-tail cross-section.

* * * * *

UNITED STATES PATENT AND TRADEMARK OFFICE
CERTIFICATE OF CORRECTION

PATENT NO. : 4,938,772
DATED : July 3, 1990
INVENTOR(S) : OTTO FREY, et al

It is certified that error appears in the above-identified patent and that said Letters Patent is hereby corrected as shown below:

```
In the Abstract, line 10 change "accidential" should be
      -accidental-
Column 1, line 64 change "meah" to -mesh-
Column 2, line 18 change "foe" to -for-
Column 2, line 36 change "Fig. 1. Referring" to -Fig. 1.
      (new paragraph) Referring...-
Column 2, line 37 change "in generally" to -in a generally-
Column 3, line 6 change "thickness" to -thicknesses-
Column 3, line 39 change "an" to -on-
Column 4, line 9 change "into" to -into said-
Column 4, line 17 change "increasing in" to -increasing thickness
      in-
Column 4, line 23 change "peg-like on" to -peg-like projection
      on-
Column 4, line 29 change "an" to -on-
Column 4, line 29 change "ars" to -arcs-
```

Signed and Sealed this

Eleventh Day of May, 1993

Attest:

MICHAEL K. KIRK

Attesting Officer

Acting Commissioner of Patents and Trademarks